United States Patent
Kim et al.

(10) Patent No.: US 11,360,093 B2
(45) Date of Patent: Jun. 14, 2022

(54) COLORECTAL CANCER DIAGNOSTIC COMPOSITION, AND METHOD FOR DETECTING DIAGNOSTIC MARKER

(71) Applicant: MEDICINAL BIOCONVERGENCE RESEARCH CENTER, Suwon-si (KR)

(72) Inventors: Sunghoon Kim, Seoul (KR); Min Chul Park, Seongnam-si (KR); Peter Charles Goughnour, Suwon-si (KR)

(73) Assignee: MEDICINAL BIOCONVERGENCE RESEARCH CENTER, Suwon-Si (KR)

(*) Notice: Subject to any disclaimer, the term of this patent is extended or adjusted under 35 U.S.C. 154(b) by 399 days.

(21) Appl. No.: 16/111,087

(22) Filed: Aug. 23, 2018

(65) Prior Publication Data

US 2019/0018015 A1    Jan. 17, 2019

Related U.S. Application Data

(63) Continuation-in-part of application No. PCT/KR2017/002081, filed on Feb. 24, 2017.

(30) Foreign Application Priority Data

Feb. 25, 2016 (KR) .................. 10-2016-0022470

(51) Int. Cl.
*G01N 31/00* (2006.01)
*G01N 33/53* (2006.01)
*G01N 33/574* (2006.01)
*C12Q 1/68* (2018.01)
*C12Q 1/6886* (2018.01)

(52) U.S. Cl.
CPC ......... *G01N 33/57419* (2013.01); *C12Q 1/68* (2013.01); *C12Q 1/6886* (2013.01); *G01N 33/574* (2013.01); *C12Q 2600/106* (2013.01); *C12Q 2600/158* (2013.01); *G01N 2333/9015* (2013.01)

(58) Field of Classification Search
None
See application file for complete search history.

(56) References Cited

U.S. PATENT DOCUMENTS

| 8,669,058 B2 | 3/2014 | Liew |
| 9,945,859 B2 | 4/2018 | Kim et al. |
| 2016/0146815 A1 | 5/2016 | Lee et al. |

FOREIGN PATENT DOCUMENTS

| KR | 10-2009-0111298 | 10/2009 | |
| KR | WO 2010021415 A1 * | 2/2010 | ............. C12N 15/09 |
| KR | 10-2010-0040583 | 4/2010 | |
| KR | 10-2011-0046521 | 5/2011 | |
| KR | 10-2015-0078472 | 7/2015 | |
| WO | WO 2014/185692 A1 | 11/2014 | |
| WO | WO 2015/102341 A1 | 7/2015 | |

OTHER PUBLICATIONS

Lee et al. (J. Microbiol. Biotechnol., 2016, vol. 26, No. 2., pp. 432-4390; Published online Dec. 8, 2015). (Year: 2015).*
Tukalo et al., "Aminoacyl-tRNA synthetases as biomarkers for cancer diagnostics", Biopolymers and Cell, 2015, 31: 32.
Kim et al., "Expression of AIMP1, 2 and 3, the scaffolds for the multi-tRNA synthetase complex is downregulated in gastric and colorectal cancer", Tumori, 2011, 97: 380-385.

* cited by examiner

*Primary Examiner* — Lisa V Cook
(74) *Attorney, Agent, or Firm* — James S. Keddie; Bozicevic, Field & Francis LLP

(57) ABSTRACT

The present invention relates to a colorectal cancer diagnostic composition and method for detecting a diagnostic marker, more specifically to a colorectal cancer diagnostic composition comprising one or more mRNAs selected from the group consisting of lysyl-tRNA synthetase (KRS) and aminoacyl-tRNA synthetase complex-interacting multifunctional protein 1 (AIMP1) of a preparation for measuring protein expression levels thereof, and a method for detecting a marker form a sample obtained from a test subject in order to provide information necessary for diagnosing colorectal cancer. The colorectal cancer diagnostic marker comprising KRS and AIMP1, according to the present invention, has raised expression levels of same in the serum of a colorectal cancer patient in comparison to a normal control group. Therefore, whether colorectal cancer is present can be accurately and rapidly determined by measuring the expression levels of one or more markers selected from the group consisting of KRS and AIMP1.

8 Claims, 6 Drawing Sheets

Specification includes a Sequence Listing.

KRS

CA-19-9

COLORECTAL CANCER DIAGNOSTIC COMPOSITION, AND METHOD FOR DETECTING DIAGNOSTIC MARKER

CROSS-REFERENCE TO RELATED APPLICATIONS

The present application is a continuation-in-part of International Application No. PCT/KR2017/002081, filed on Feb. 24, 2017, which claims benefit of priority to Korean Patent Application No. 10-2016-0022470, filed on Feb. 25, 2016, the entire contents of which applications are incorporated herein by reference.

TECHNICAL FIELD

The present invention relates to a colorectal or colon cancer diagnostic composition, and a method for detecting a diagnostic marker of a colorectal or colon cancer. More specifically, the present invention relates to a composition for diagnosing a colon cancer comprising an agent for measuring a mRNA or protein level of at least one selected from the group consisting of lysyl-tRNA synthetase (KRS) and aminoacyl-tRNA synthetase complex-interacting multifunctional protein 1 (AIMP1), a method for detecting a marker of a colon cancer so as to provide information necessary for diagnosis of a colon cancer, and use of an agent for measuring a mRNA or protein level of at least one selected from the group consisting of lysyl-tRNA synthetase (KRS) and aminoacyl-tRNA synthetase complex-interacting multifunctional protein 1 (AIMP1) for the preparation of a diagnostic agent for a colon cancer.

BACKGROUND OF THE INVENTION

In 2002, the number of cancer (malignant neoplasm) deaths in the Republic of Korea was 62,887, which is 25.5% (29.6% of male deaths and 20.5% of female deaths) among a total of 246,515 deaths in the Republic of Korea (512 deaths per 100,000 population). Cancer is the number one cause of death (130.7 deaths per 100,000 population). Lung, stomach, liver, colon and pancreatic cancers predominate in order of mortality rate, while deaths from these top five cancers account for about 70% of all cancer deaths. Also, the major causes of cancer deaths in male are lung, stomach, liver and colon cancers, while the deaths from the four major cancers (28,147) account for 70% of all male cancer deaths (40,177). The major causes of cancer deaths in female are gastric, lung, liver, colon and pancreatic cancers, while the deaths from these five cancers (13,630) account for 60% of all female cancer deaths (22,710).

Colon or colorectal cancer refers to malignant tumors of the colon and rectum, with a worldwide incidence rate of 945,000 new cases (9.4% of worldwide total cancer incidence) and mortality rate of 492,000 deaths (7.9% of total cancer deaths) in 2000 is the third highest in all cancers. When compared by gender, it occurs at a similar rate in male and female (male:female 1.1:1). Because its prognosis is relatively good compared to other cancers, the survival rate for people with colon cancer is the second highest in the world after breast cancer, while estimated 2.4 million people are still alive after being diagnosed with colon cancer within the past 5 years (Parkin D M, Global cancer statistics in the year 2000, Lancet Oncol 2:533-543, 2001). The 5-year survival rate for colon cancer prognosis is 90% or higher in early stage (stage I) patients, whereas being only 5% in metastatic (stage IV) patients (Cancer Facts and Figures 2004. American Cancer Society, 2004).

In the Republic of Korea, the incidence and mortality of colon cancer have increased remarkably due to recent westernization of dietary culture. According to the annual report of the Korean Central Cancer Registry (2002. 1~2002. 12), published by the Ministry of Health and Welfare and the Korea Central Cancer Registry Office, the number of colon cancer incidence in 2002 was 11,097, the fourth most common cancer, accounting for 11.2% of all cancer incidence. By gender, there were 6,423 male cases, more frequent than female cases (4,647), while by age, 60s (3,751) are the most common, followed by 50s (2,400). The incidence of colon cancer has been increasing steadily for the past four years from 1999 to 2002, in 2002 compared to 1999, the crude incidence rate of cancer (the number of new cancer per 100,000 population) has increased by 36.4% from 22.5 to 30.7 in male, and by 22.9% from 18.8 to 23.1 in female, leading to its overall increase by 30.6% from 20.6 to 26.9 (Survival rate of cancer patients in 1993-2002 and Cancer Incidence in 1993-2002, Ministry of Health and Welfare, 2007. 7). In 2006, among a total of 6,277 people died of colon cancer, the fourth ranked (9.5%) cancer deaths, there were 3,453 male deaths in fourth place (8.0%), and 2,824 female deaths in third place (11.5%). Also, colon cancer is the most common cancer with the highest mortality rate in the last decade after lung cancer (2006 statistics on death and its causes, Statistics Korea, 2007. 9).

In the case of colon cancer, since its development is slow from a pre-cancerous lesion that can be removed or from an early-stage cancer that can be treated, screening for colon cancer has a potential to reduce its incidence and mortality rates. It is believed that screening for colon cancer in both male and female over the age of 50 can reduce colon cancer mortality (Walsh J M & Terdiman J P, JAMA 289: 1288-96, 2003). However, compliance and supply rates for colonoscopy, the most reliable screening method currently available, are low. Oppositely, the fecal occult blood test (FOBT), the most widely used non-invasive screening option, has several important limitations, including its low sensitivity above all. In the United States, only 40% of adults over age 50 in 2002 received colonoscopy within the past 5 years, and only 22% received fecal occult blood test within the past 12 months (Behavior risk factor survey, National center for chronic disease prevention and health promotion. Centers for disease control and prevention, 2002). Participation rates for screening tests for colon cancer are lower than those for breast and cervical cancers, due to various factors, including patient discomfort, cost, lack of awareness, and low acceptance of current screening methods.

Therefore, it is very important to develop a new marker for early diagnosis of colon cancer in an accurate and rapid manners.

DETAILED DESCRIPTION OF THE INVENTION

Technical Problem

Accordingly, the present inventors have completed the present invention after they have found a biomarker which can be detected simply and rapidly in the serum of colon cancer patients and has a high sensitivity and specificity, as a result of efforts to develop a biomarker capable of effectively diagnosing colon cancer.

Accordingly, an aspect of the present invention is to a composition for diagnosing a colon cancer comprising an agent for measuring a mRNA or protein level of at least one selected from the group consisting of lysyl-tRNA synthetase (KRS) and aminoacyl-tRNA synthetase complex-interacting multifunctional protein 1 (AIMP1).

Another aspect of the present invention is to provide a kit for diagnosing a colon cancer comprising an agent for measuring a mRNA or protein level of at least one selected from the group consisting of lysyl-tRNA synthetase (KRS) and aminoacyl-tRNA synthetase complex-interacting multifunctional protein 1 (AIMP1).

Another aspect of the present invention is to provide a method for diagnosing and treating a colon cancer in a subject, the method comprising the steps of:
(a) obtaining a sample from a subject;
(b) measuring a mRNA or protein level of at least one selected from the group consisting of lysyl-tRNA synthetase (KRS) and aminoacyl-tRNA synthetase complex-interacting multifunctional protein 1 (AIMP1) in the sample;
(c) comparing the mRNA or protein level in the sample with a mRNA or protein level of a normal control sample of a healthy subject;
(d) diagnosing the subject with a colon cancer when the mRNA or protein level from the sample of the subject is greater than that of the normal control sample of the healthy subject; and
(e) treating the diagnosed subject by at least one of (i) administering an effective amount of a therapeutic agent for colon cancer to the diagnosed subject, (ii) conducting a curative surgery, and (iii) conducting a radiation therapy.

Another aspect of the present invention is to provide a method for screening an anti-colon cancer agent, the method comprising the steps of:
(a) administering an anti-colon cancer agent candidate to a sample obtained from a colon cancer patient;
(b) measuring a mRNA or protein level of at least one selected from the group consisting of lysyl-tRNA synthetase (KRS) and aminoacyl-tRNA synthetase complex-interacting multifunctional protein 1 (AIMP1) in the sample under the presence or absence of the anti-colon cancer agent candidate;
(c) comparing the mRNA or protein level under the presence of the candidate with the mRNA or protein level under the absence of the candidate;
(d) selecting the candidate that decreases the mRNA or protein level under the presence of the candidate; and
(e) determining the anticancer activity of the selected candidate in a cell or an animal.

Another aspect of the present invention is to provide use of an agent for measuring a mRNA or protein level of at least one selected from the group consisting of lysyl-tRNA synthetase (KRS) and aminoacyl-tRNA synthetase complex-interacting multifunctional protein 1 (AIMP1) for the preparation of a diagnostic agent for a colon cancer.

Technical Solution

An embodiment according to an aspect of the present invention provides a composition for diagnosing a colon cancer comprising an agent for measuring a mRNA or protein level of at least one selected from the group consisting of lysyl-tRNA synthetase (KRS) and aminoacyl-tRNA synthetase complex-interacting multifunctional protein 1 (AIMP1).

An embodiment according to another aspect of the present invention provides a kit for diagnosing a colon cancer comprising an agent for measuring a mRNA or protein level of at least one selected from the group consisting of lysyl-tRNA synthetase (KRS) and aminoacyl-tRNA synthetase complex-interacting multifunctional protein 1 (AIMP1).

An embodiment according to another aspect of the present invention provides a method for diagnosing and treating a colon cancer in a subject, the method comprising the steps of:
(a) obtaining a sample from a subject;
(b) measuring a mRNA or protein level of at least one selected from the group consisting of lysyl-tRNA synthetase (KRS) and aminoacyl-tRNA synthetase complex-interacting multifunctional protein 1 (AIMP1) in the sample;
(c) comparing the mRNA or protein level in the sample with a mRNA or protein level of a normal control sample of a healthy subject;
(d) diagnosing the subject with a colon cancer when the mRNA or protein level from the sample of the subject is greater than that of the normal control sample of the healthy subject; and
(e) treating the diagnosed subject by at least one of (i) administering an effective amount of a therapeutic agent for colon cancer to the diagnosed subject, (ii) conducting a curative surgery, and (iii) conducting a radiation therapy.

An embodiment according to another aspect of the present invention provides a method for screening an anti-colon cancer agent, the method comprising the steps of:
(a) administering an anti-colon cancer agent candidate to a sample obtained from a colon cancer patient;
(b) measuring a mRNA or protein level of at least one selected from the group consisting of lysyl-tRNA synthetase (KRS) and aminoacyl-tRNA synthetase complex-interacting multifunctional protein 1 (AIMP1) in the sample under the presence or absence of the anti-colon cancer agent candidate;
(c) comparing the mRNA or protein level under the presence of the candidate with the mRNA or protein level under the absence of the candidate;
(d) selecting the candidate that decreases the mRNA or protein level under the presence of the candidate; and
(e) determining the anticancer activity of the selected candidate in a cell or an animal.

An embodiment according to another aspect of the present invention provides use of an agent for measuring a mRNA or protein level of at least one selected from the group consisting of lysyl-tRNA synthetase (KRS) and aminoacyl-tRNA synthetase complex-interacting multifunctional protein 1 (AIMP1) for the preparation of a diagnostic agent for a colon cancer.

Hereinafter, the present invention will be described in detail.

The present invention provides a composition for diagnosing a colon cancer comprising an agent for measuring a mRNA or protein level of at least one selected from the group consisting of lysyl-tRNA synthetase (KRS) and aminoacyl-tRNA synthetase complex-interacting multifunctional protein 1 (AIMP1).

The present inventors were the first to confirm that KRS and AIMP1 were significantly increased in colon cancer patients than normal controls, and that they are highly valuable as new colon cancer diagnostic markers.

In another embodiment of the present invention, through the ROC curve analysis of KRS (lysyl-tRNA synthetase) and AIMP1 (aminoacyl-tRNA synthetase complex-interacting multifunctional Protein 1), each of the markers was found to have excellent sensitivity and specificity in diagnosing colon cancer. The sensitivity and specificity of the diagnostic markers according to the present invention were significantly superior to these of CA19-9, one of the conventional colon cancer diagnostic markers.

Based on the above findings of the present inventors, the present invention provides a composition for diagnosing colon cancer comprising an agent for measuring the expression level of lysyl-tRNA synthetase (KRS) and/or aminoacyl-tRNA synthetase complex-interacting multifunctional Protein 1 (AIMP1), that is, the protein or mRNA level of KRS and/or AIMP1.

Aminoacyl-tRNA synthetase (ARS) is an enzyme that attaches a specific amino acid to its corresponding tRNA. In the case of higher organisms, in addition to 20 enzymes according to the type of amino acid, it is composed of 23 enzymes including three enzymes involved in the formation of multisynthetase complexes such as AIMP1 (p43), (AIMP2) p38, and (AIMP3) p18. In addition to the enzymes involved in the formation of multisynthetase complexes, some enzymes also exist in a free form. However, in recent years, it has been reported that in addition to their basic functions, some of the enzymes including KRS and AIMP1 possess various other functions in a specific environment.

KRS was shown to induce an immune response through macrophage activation. KRS, which is extra cellularly secreted by TNF-α, has been reported to increase the activity of macrophage cells by TNF-α by signaling via p38 mitogen activated kinase and the like, or to promote cell migration. KRS has also recently been shown to be involved in a variety of diseases. It has been reported that autologous antibodies to KRS are present in patients with inflammatory muscle diseases, while KRS is involved in binding to SOD1 enzyme in a patient with SOD1 gene mutation causing Lou Gehrig's disease. However, it has not been known that KRS can be used as a diagnostic marker for colon cancer because its protein level in the serum of colon cancer patients is significantly higher than that of normal control subjects, while such findings are first disclosed in the present invention.

AIMP1 (ARS-interacting multi-functional protein 1) is a protein previously known as p43 protein and recently renamed as AIMP1 (Sang Gyu Park, et al., Trends in Biochemical Sciences, 30:569-574, 2005). The AIMP1 is a protein consisting of 312 amino acids, which binds to a multi-tRNA synthetase complex (Deutscher, M. P., Method Enzymol, 29, 577-583, 1974; Dang C. V. et al., Int. J. Biochem. 14, 539-543, 1982; Mirande, M. et al., EMBO J. 1, 733-736, 1982; Yang D. C. et al., Curr. Top Cell. Regul. 26, 325-335, 1985) and promotes the catalytic activity of the multi-tRNA synthetase (Park S. G. et al., J. Biol. Chem. 274, 16673-16676, 1999). Secreted AIMP1 is known to act on a variety of target cells such as monocytes/macrophages, endothelial cells and fibroblasts. However, it has not been known that AIMP1 can be used as a diagnostic marker for colon cancer because its protein level in the serum of colon cancer patients is significantly higher than that of normal control subjects, while such findings are first disclosed in the present invention.

As used herein, the terms 'diagnostic marker', 'marker for diagnosis' or 'diagnosis marker' refer to a substance or an agent that can diagnose by distinguishing colon cancer patients from normal controls, including an organic biomolecule such as a polypeptide or a nucleic acid (e.g. mRNA or the like), a lipid, a glycolipid, a glycoprotein or a sugar (monosaccharide, disaccharide, oligosaccharide and the like), which shows an increase or decrease in the colon cancer patients as compared with the normal controls. For the purpose of the present invention, the colon cancer diagnostic marker of the present invention is KRS (lysyl-tRNA synthetase) or AIMP1 (aminoacyl-tRNA synthetase complex-interacting multifunctional Protein 1) genes and proteins encoded thereby, which specifically show higher expression levels in cancer cells as compared with cells of normal tissue.

As used herein, the term 'expression' means that a protein or a nucleic acid is produced in a cell. The term 'protein' is used interchangeably with 'polypeptide' or 'peptide' and for example, refers to a polymer of amino acid residues as commonly found in naturally occurring proteins. The term 'polynucleotide' or 'nucleic acid' refers to deoxyribonucleotide (DNA) or ribonucleotide (RNA) in the form of single strand or double strands. Unless otherwise limited, it also includes known analogs of natural nucleotides that hybridize to nucleic acids in a manner similar to naturally occurring nucleotides. The term 'mRNA' is a RNA that transfers genetic information (gene-specific nucleotide sequence) to ribosomes that specify amino acid sequences from a specific gene during protein synthesis.

The term 'diagnosis' means identifying the presence or characteristics of a pathological condition. The diagnosis as used herein is to determine the expression level of the KRS and/or AIMP1 gene, that is, the protein or mRNA level of one or more of the markers is measured to ascertain the existence of pathological incidence or development of colon cancer.

Meanwhile, when the diagnostic composition of the present invention is used for measuring the expression level of mRNA, the agent for measuring mRNA expression level may be a probe or a primer set that specifically binds to mRNA of KRS and/or AIMP1.

The KRS and AIMP1 mRNA may be derived form a mammal including a human, preferably the mRNA of KRS comprising the nucleotide sequence of SEQ ID NO: 1 and the mRNA of AIMP1 comprising the nucleotide sequence of SEQ ID NO: 2. The diagnostic composition of the present invention, comprising a probe or primer set specific for mRNA of at least one selected from the group consisting of KRS and AIMP1 as an agent for measuring the expression level of at least one selected from the group consisting of KRS and AIMP1, may further comprise an agent necessary for known methods of detecting RNAs. The known methods of detecting RNAs using the composition according to the present intention may be used without limitation to determine the mRNA level of the markers in a subject.

The term 'primer' refers to a short single strand oligonucleotide that acts as a starting point for DNA synthesis. The primer specifically binds to a polynucleotide as a template under suitable buffer and temperature conditions, and DNA is synthesized by the addition of nucleoside triphosphate having a base complementary to the template DNA by DNA polymerase. The primer is generally composed of 15 to 30 nucleotide sequences, and a melting temperature (Tm) at which the primer binds to the template strand varies depending on the composition and length of bases.

Being unnecessary to be completely complementary to a partial nucleotide sequence of the template, it is sufficient that the complementary nucleotide has sufficient complementarity within a range enough to hybridize with the template and acting as a primer. Therefore, the primer for measuring the mRNA level of the above markers in the present invention does not need to have a sequence completely complementary to its corresponding gene sequence, while it is sufficient that the primer has a sequence length and complementary appropriate for the purpose of measuring the mRNA level by amplifying a particular region of mRNA or cDNA through DNA synthesis. The primer for such an amplification reaction is composed of a set (pair) of strands complementarily binding to a template (or sense) strand and an opposite (antisense) strand at the ends of a specific region of the mRNA to be amplified, respectively. Primers can be easily designed by those skilled in the art with reference to the KRS or AIMP1 mRNA or cDNA sequence.

The primer of the present invention is preferably a set, a pair or combination thereof which specifically binds to the nucleotide sequence of KRS mRNA of SEQ ID NO: 1 or the nucleotide sequence of AIMP1 mRNA of SEQ ID NO: 2, most preferably at least one forward primer selected from the group consisting of SEQ ID NO: 5 and SEQ ID NO: 6, and at least one reverse primer selected from the group consisting of SEQ ID NO: 7 and SEQ ID NO: 8, while being not limited thereto. As used herein, SEQ ID NO: 5 and SEQ ID NO: 7 are primers specific to the nucleotide sequence of KRS mRNA, while SEQ ID NO: 6 and SEQ ID NO: 8 are primers specific the nucleotide sequence of AIMP1 mRNA.

The term 'probe' refers to a fragment of a polynucleotide, such as RNA or DNA having a base pair length of several to several hundreds, which can specifically bind to mRNA or cDNA (complementary DNA) of a specific gene, while the probe is labeled so that the presence or expression level of mRNA or cDNA to be bound can be confirmed. For the purpose of the present invention, probes complementary to KRS or AIMP1 mRNA may be used for the diagnosis of colon cancer by measuring the mRNA level of KRS of AIMP1 through performing hybridization with a sample of a subject. The selection and hybridization conditions of the probes can be appropriately determined according to techniques known in the art.

The primer or probe of the present invention can be chemically synthesized using a phosphoramidite solid support synthesis method or other well-known methods. In addition, the primer or probe may be modified in various ways according to methods known in the art, so long as it does not interfere with its hybridization with mRNA of KRS of AIMP1. Examples of such modifications include, but are not limited to, methylation, capping, substitution with one or more of the natural nucleotide analogs, and modifications between nucleotides such as the binding of labeling materials using uncharged linkers (e.g., methylphosphonate, phosphotriester, phosphoramidate, and carbamate) or charged linkers (e.g., phosphorothioate, and phosphorodithioate), and fluorescences or enzymes.

When the diagnostic composition of the present invention is used for measuring a protein level, the agent for measuring the protein level may be an antibody that specifically binds to KRS or AIMP1 protein, respectively.

The KRS and AIMP1 protein may be derived form a mammal including a human, preferably the KRS protein comprises the amino acid sequence of SEQ ID NO: 3 and the AIMP1 protein comprises the amino acid sequence of SEQ ID NO: 4, respectively.

The term 'antibody' means an immunoglobulin that specifically binds to an antigenic site. The antibody according to the present invention does not react with other proteins including different types of ARS other than the KRS or AIMP1, and specifically binds only to the KRS or AIMP1 protein. The KRS or AIMP1 antibody may be produced by cloning each gene into an expression vector to obtain a protein encoded by the gene, followed by its preparation from the obtained protein according to a conventional method in the art. A fragment of KRS or AIMP1 protein comprising a KRS or AIMP1 antigenic site may be used to prepare antibodies specific to each of said proteins. The form of the antibody of the present invention is not particularly limited and includes a polyclonal antibody and a monoclonal antibody. In addition, the antibody according to the present invention includes a portion of whole antibody as long as it has an antigen-antibody binding property. Some of the whole antibodies are also included in the antibodies of the present invention, while including all kinds of immunoglobulin antibodies that specifically bind to the KRS or AIMP1. For example, it includes an antibody in complete form having two full-length light chains and two full-length heavy chains, as well as functional fragments of antibody molecules, that is, Fab, F(ab'), F(ab')2 and Fv having an antigen binding function. Further, the antibody of the present invention includes a specific antibody such as a humanized antibody, a chimeric antibody, and a recombinant antibody as long as it can specifically bind to the KRS of AIMP1 protein.

The diagnostic composition of the present invention, which comprises each of the marker protein-specific antibodies as an agent for measuring the expression level of KRS or AIMP1, may further comprise an agent necessary for a known method for detecting a protein. The known method of detecting proteins using the present composition may be used without limitation to determine the level of one or more proteins selected from the group consisting of KRS and AIMP1 in a subject.

Also, the present invention provides a kit for diagnosing a colon cancer comprising an agent for measuring a mRNA or protein level of at least one selected from the group consisting of lysyl-tRNA synthetase (KRS) and aminoacyl-tRNA synthetase complex-interacting multifunctional protein 1 (AIMP1).

The diagnostic kit of the present invention may comprise one or more other compositions, solutions or devices suitable for assay, as well as antibodies selectively recognizing at least one protein selected from the group consisting of KRS and AIMP1 as a marker, primers and probes that recognize mRNA of at least one selected from the group consisting of KRS and AIMP1 as a marker.

According to a specific embodiment, the diagnostic kit may be a diagnostic kit comprising essential elements necessary for performing a reverse transcription polymerase chain reaction (RT-PCR). A RT-PCR kit contains a pair of primers specific for each marker gene. The primer is a nucleotide having a sequence specific to the nucleic acid sequence of each marker gene, with about 7 bp to 50 bp in length, more preferably about 10 bp to 30 bp in length. It may also contain a primer specific for the nucleic acid sequence of a control gene. Other RT-PCR kits may comprise test tubes or other appropriate containers, reaction buffers (with varying pH and magnesium concentrations), deoxynucleotides (dNTPs), enzymes such as Taq polymerase and reverse transcriptase, DNAse, RNAse inhibitor DEPC-treated water, and sterile water.

Another embodiment of the present invention may provide a diagnostic kit characterized by comprising essential elements necessary for operating a DNA chip. The DNA chip kit may comprise a substrate on which a cDNA or oligonucleotide corresponding to a gene or a fragment thereof is attached, reagents, preparations, and enzymes for producing a fluorescent-labeled probe. The substrate may also comprise a cDNA or oligonucleotide corresponding to a control gene or fragment thereof.

Most preferably, another embodiment of the present invention may provide a diagnostic kit characterized by comprising essential elements necessary for performing an ELISA. ELISA kits contain antibodies specific for a marker protein. Antibodies as used include monoclonal, polyclonal or recombinant antibodies with high specificity and affinity for each marker protein and little cross reactivity to other proteins. The ELISA kits may also comprise antibodies specific for a control protein. The ELISA kits may further comprise reagents capable of detecting bound antibodies, such as labeled secondary antibodies, chromophores, enzymes (in a conjugated form with antibodies) and their substrates or other substances capable of binding to antibodies. In addition, the kit of the present invention may comprise washing or eluting solutions by which substrates to be color-developed with enzymes and unbound proteins are removed, while bound protein markers are only retained.

The sample used for the analysis includes a biological sample capable of identifying a cancer-specific protein that can be distinguished from a healthy state, such as blood, serum, urine, tear, and saliva. Preferably the analysis may be conducted by measuring from biological liquid samples, such as blood, serum, and plasma. The sample may be prepared to enhance the detection sensitivity of a protein marker. For example, a serum sample obtained from a patient can be pre-treated using such methods as anion exchange chromatography, affinity chromatography, size exclusion chromatography, liquid chromatography, sequential extraction and gel electrophoresis.

The present invention also provides a method for diagnosing and treating a colon cancer in a subject, the method comprising the steps of:
 (a) obtaining a sample from a subject;
 (b) measuring a mRNA or protein level of at least one selected from the group consisting of lysyl-tRNA synthetase (KRS) and aminoacyl-tRNA synthetase complex-interacting multifunctional protein 1 (AIMP1) in the sample;
 (c) comparing the mRNA or protein level in the sample with a mRNA or protein level of a normal control sample of a healthy subject;
 (d) diagnosing the subject with a colon cancer when the mRNA or protein level from the sample of the subject is greater than that of the normal control sample of the healthy subject; and
 (e) treating the diagnosed subject by at least one of (i) administering an effective amount of a therapeutic agent for colon cancer to the diagnosed subject, (ii) conducting a curative surgery, and (iii) conducting a radiation therapy.

The inventors first discovered that the KRS and AIMP1 can function as a novel marker of a colon cancer and provided a method for measuring the expression level of each markers to provide information necessary for the diagnosis of a colorectal or colon cancer. Hereinafter, the method of the present invention will be described in a sequential manner.

Step (a) of the method according to the present invention is a step of obtaining a sample from a subject.

The sample can be used without limitation as long as it is collected from a subject to be diagnosed as having a colorectal or colon cancer. For example, the sample may be a cell or tissue obtained by biopsy, blood, whole blood, serum, plasma, saliva, cerebrospinal fluid, various secretions, urine, feces and the like. Preferably, the sample may be blood, plasma, serum, saliva, nasal mucus, sputum, capsular fluid, amniotic fluid, ascites, cervical or vaginal discharge, urine or cerebrospinal fluid. Most preferably, the sample may be blood, plasma, or serum.

Step (b) of the method according to the present invention is a set of measuring the expression level of at least one selected from the group consisting of lysyl-tRNA synthetase (KRS) and aminoacyl-tRNA synthetase complex-interacting multifunctional protein 1 (AIMP1) in the sample provided in step (a). The expression level may be a mRNA or protein level of at least one selected from the group consisting of KRS and AIMP1.

The level of each protein may be detected or measured using an antibody that specifically binds to each protein. The protein-specific antibody is as described above for the diagnostic composition of the present invention. Methods known in the art for measuring the level of each protein can be used without limitation, and examples thereof include Western blotting, dot blotting, enzyme-linked immunosorbent assay (ELISA), radioimmunoassay (RIA), radioimmunodiffusion, ouchterlony immunodiffusion, rocket immuno-electrophoresis, immunohistostaining, immunoprecipitation assay, complement fixation assay, FACS, and protein chip, but are not limited thereto. Preferably, an ELISA method may be used.

Regarding the mRNA levels of each markers, the existence and level of the mRNA of each markers in a sample of the subject can be determined by amplifying the mRNA or cDNA of each markers from a sample of the subject using a primer set or a probe that specifically binds to the mRNA of each markers or by using hybridization with a probe. The primers and probes are the same as described above in the diagnostic composition of the present invention. The measurement of the mRNA level can be performed by methods known in the art without any limitations. For example, reverse transcription polymerase chain reaction (RT-PCR), competitive RT-PCR, real-time RT-PCR, RNase protection assay (RPA), northern blotting, DNA microarray chip, RNA sequencing, hybridization using nanostring, and in situ hybridization of tissue sections, but are not limited thereto.

Step (c) of the method of the present invention is a step of comparing the mRNA or protein level selected from the group consisting of KRS and AIMP1 of the test sample measured in step (b) with a mRNA or protein level of a normal control sample of a healthy subject, followed by step (d) diagnosing the subject with a colon cancer when the mRNA or protein level from the sample of the subject is greater than that of the normal control sample of the healthy subject; and step (e) treating the diagnosed subject by at least one of (i) administering an effective amount of a therapeutic agent for colon cancer to the diagnosed subject, (ii) conducting a curative surgery, and (iii) conducting a radiation therapy.

The expression level of each markers of the subject measured by step (b) described above is compared with that of the healthy subject measured in the same manner. If the expression level of each markers is increased compared to a normal healthy subject, the subject is determined to have a colon cancer.

The present invention also provides a method for screening an anti-colon cancer agent, the method comprising the steps of:
 (a) administering an anti-colon cancer agent candidate to a sample obtained from a colon cancer patient;
 (b) measuring a mRNA or protein level of at least one selected from the group consisting of lysyl-tRNA synthetase (KRS) and aminoacyl-tRNA synthetase complex-interacting multifunctional protein 1 (AIMP1) in the sample under the presence or absence of the anti-colon cancer agent candidate;

(c) comparing the mRNA or protein level under the presence of the candidate with the mRNA or protein level under the absence of the candidate;

(d) selecting the candidate that decreases the mRNA or protein level under the presence of the candidate; and (e) determining the anticancer activity of the selected candidate in a cell or an animal.

Specifically, the method can be useful for screening a therapeutic agent for colon cancer by comparing the increase or decrease of a mRNA or protein level of at least one selected from the group consisting of KRS and AIMP1 under the presence and absence of an anti-colon cancer agent candidate. Any candidate that indirectly or directly reduces the mRNA or protein level of at least one selected the group consisting of KRS and AIMP1 may be selected as a therapeutic agent for colon cancer. That is, the expression level of the marker of the present invention in colon cancer cells is measured under the absence of the anti-colon cancer agent candidate, while the expression level of the marker of the present invention is measured under the presence of the anti-colon cancer agent candidate, followed by the comparison of measured levels. Then, if the expression level of the marker of the present invention in the presence of the anti-colon cancer agent candidate is lower than the level in the absence of the anti-colon cancer agent candidate, said candidate may be selected as a therapeutic agent for colon cancer.

As used herein, the 'anticancer activity' means an activity of inhibiting an increased abnormal cell division, transformation from normal cells into cancer cells, cell division and proliferation of cancer cells, development and growth of tumors, and the like.

As used herein, the 'cell or animal' may be a cell or an animal of a cancer or tumor model. As commonly used in the art, it may be a cell, a tissue, an organ, etc. derived from an animal such as a mammal including a human.

The present invention provides use of an agent for measuring a mRNA or protein level of at least one selected from the group consisting of KRS (lysyl-tRNA synthetase) and AIMP1 (aminoacyl-tRNA synthetase complex-interacting multifunctional protein 1) for preparing an agent for diagnosis of a colon cancer.

As used herein, the agent for measuring the mRNA level may be a probe or a primer set that specifically binds to mRNA of KRS or AIMP1, as described above.

As used herein, the agent for measuring the protein level may be an antibody specific for the KRS or AIMP1 protein, as described above.

As described above, the mRNA of KRS may comprise the nucleotide sequence of SEQ ID NO: 1, while the mRNA of AIMP1 may comprise the nucleotide sequence of SEQ ID NO: 2. The KRS protein may comprise the amino acid sequence of SEQ ID NO: 3, while the AIMP1 protein may comprise the amino acid sequence of SEQ ID NO: 4.

An embodiment of the present invention provides the use of an agent for measuring a mRNA or protein level of at least one selected from the group consisting of KRS and AIMP1 for preparing a colon cancer diagnostic kit. The kit of the present invention may be a RT-PCR kit, a DNA chip kit, or a protein chip kit, but is not limited thereto.

Advantageous Effect

The colon cancer diagnostic markers of KRS and AIMP1 according to the present invention are found to have increased expression levels in the serum of colon cancer patients compared with the normal control. Therefore, by measuring the expression levels of at least one markers selected from the group consisting of KRS and AIMP1, the presence or absence of colon cancer can be accurately and rapidly verified.

BRIEF DESCRIPTION OF DRAWINGS/FIGURES

MODE FOR CARRYING OUT INVENTION

Figure 1A:
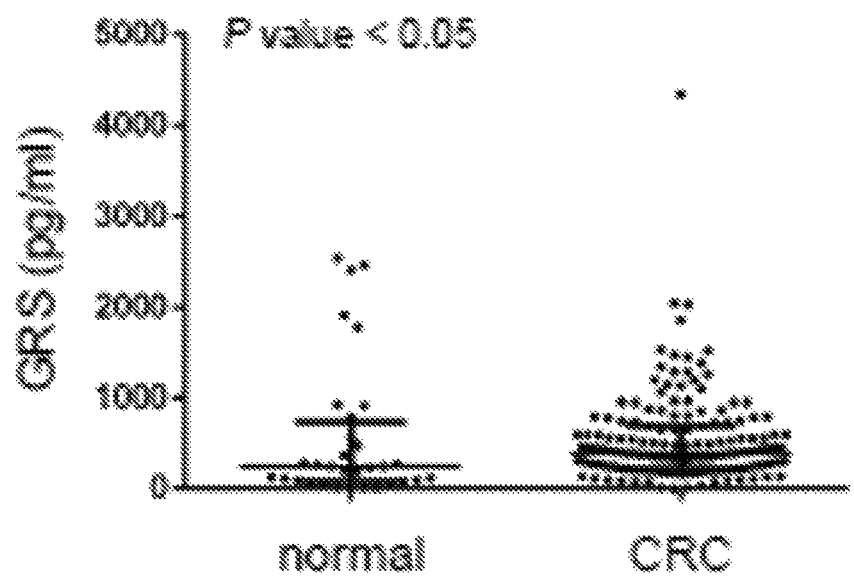
FIGS. 1A, 1B, 1C, 1D, 1E, 1F, 1G and 1H show the serum protein levels of colon cancer patients and normal controls by dot blot, respectively (A: GRS, B: KRS, C: AIMP1, D: HRS, E: WRS, F: CA-19-9, G: TNF-α, H: IL-10).
Figure 1B:
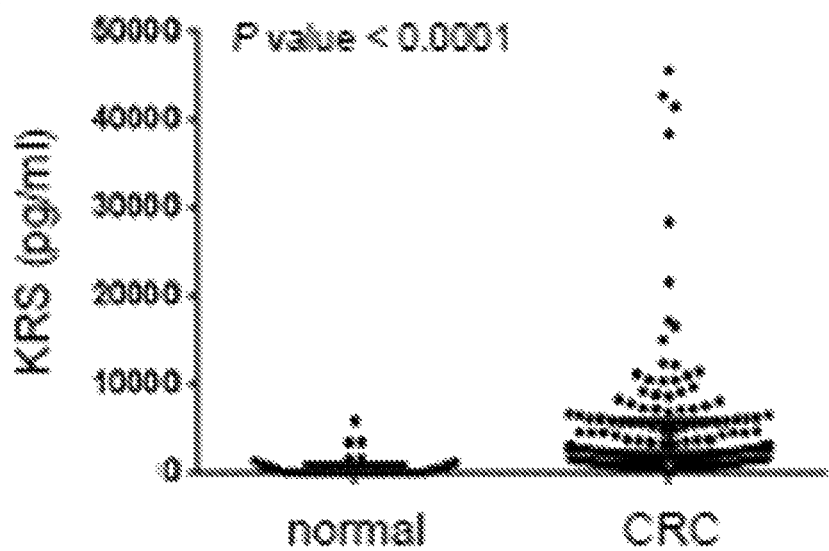
Figure 1C:
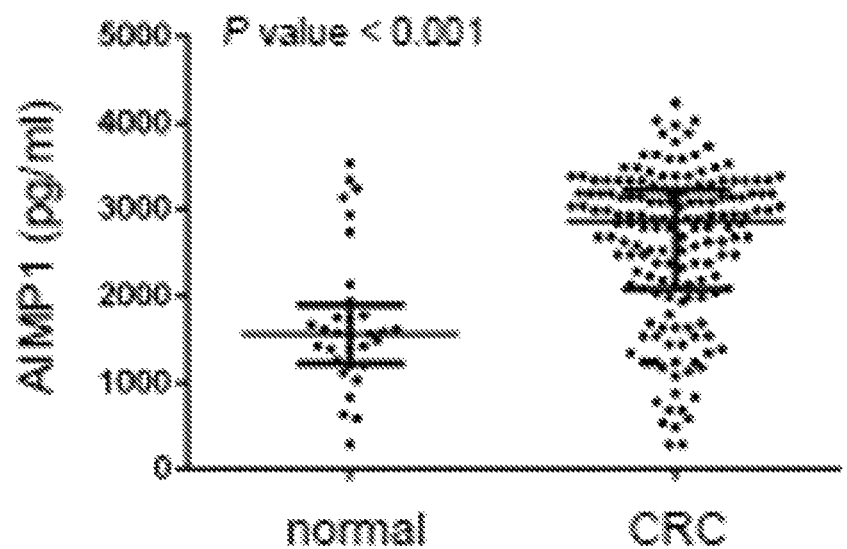
Figure 1D:
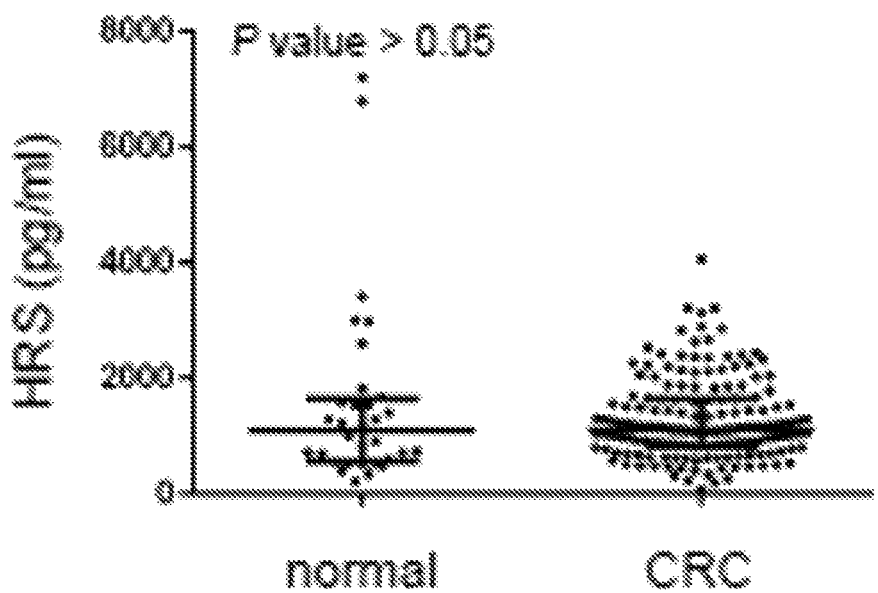
Figure 1E:
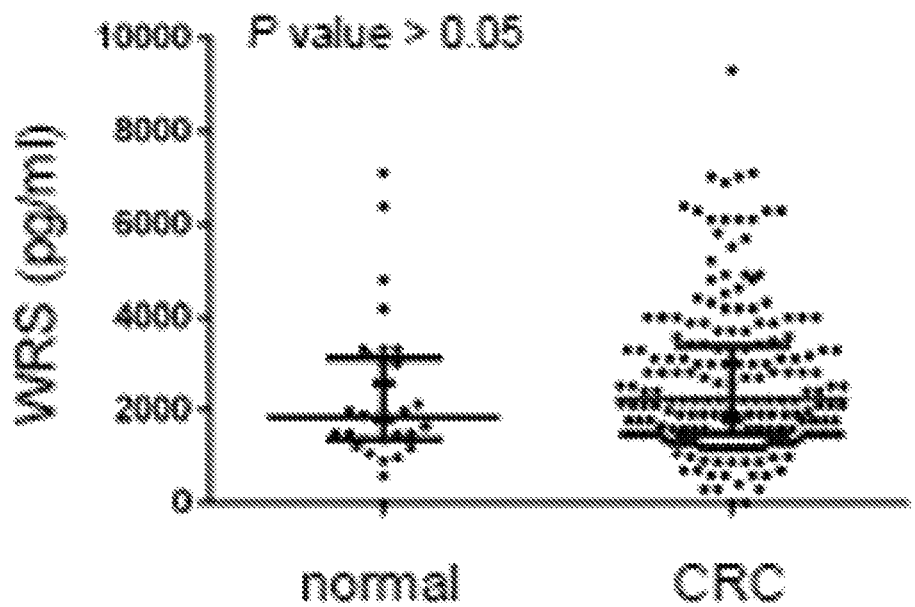
Figure 1F:
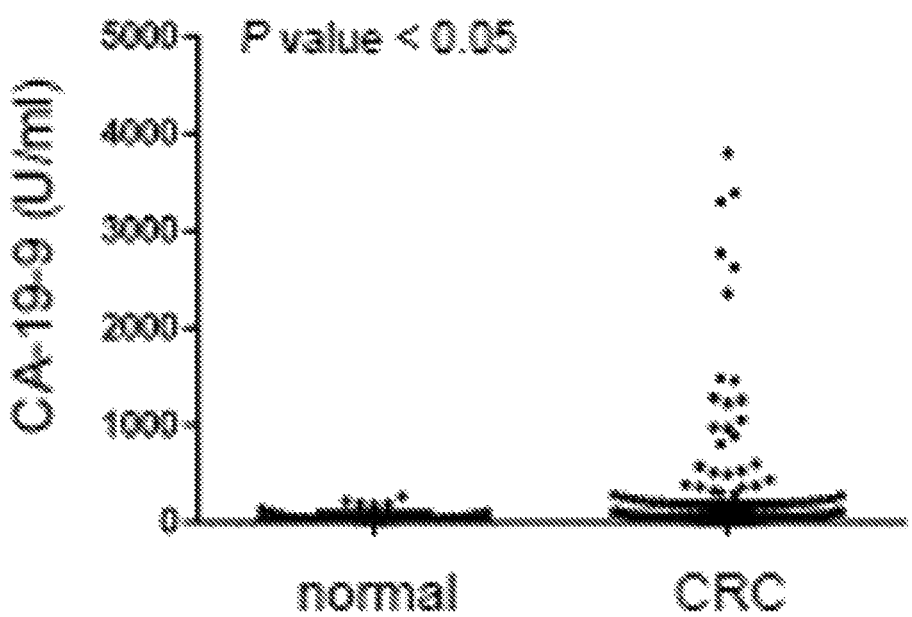
Figure 1G:
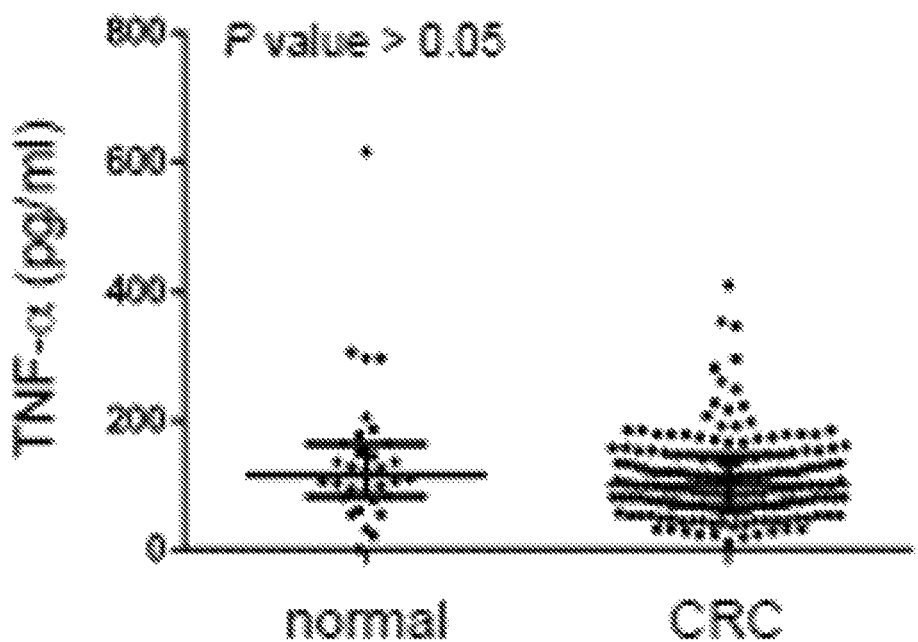
Figure 1H:
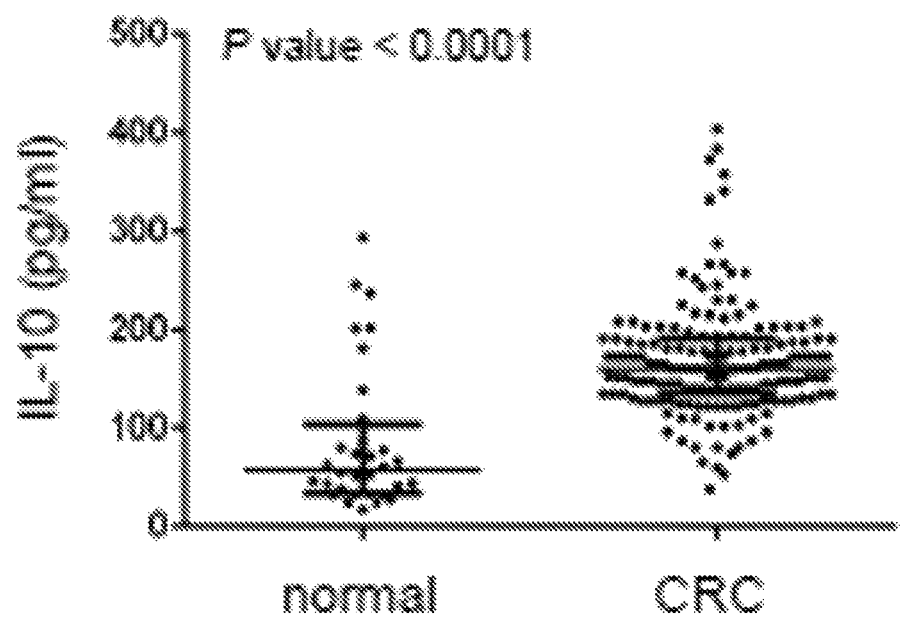

Hereinafter, the present invention will be described in detail.

However, the following examples are illustrative of the present invention, and the present invention is not limited to the following examples.

Methods

1. Obtaining of Experimental Samples

Serum from colon cancer patients was obtained from the Samsung Medical Center (Seoul, Republic of Korea) according to the regulations of the Clinical Examination Committee. Samples of 32 normal controls and 164 colon cancer patients were obtained and analyzed.

The clinical information of the subjects participated in the experiment is as shown in Table 1.

TABLE 1

Clinical and pathologic information of normal controls and colon cancer patients

|  |  | Normal controls | Colon cancer patients |
|---|---|---|---|
| Number of subjcects |  | 32 | 164 |
| Gender | Male | 20 | 93 |
|  | Female | 12 | 71 |
| Average age |  | 44.33 ± 9.27 | 60.2 ± 12.2 |
| Tumor stage | Stage I | — | 14 |
|  | Stage II | — | 50 |
|  | Stage III | — | 50 |
|  | Stage IV | — | 50 |
| Timor size(cm) |  |  | 5.75 ± 1.89 |

2. ELISA Assay

The level of GRS (glycyl-tRNA synthetase), KRS (lysyl-tRNA synthetase), HRS (histidyl-tRNA synthetase), WRS (tryptophanyl-tRNA synthetase), AIMP-1 (aminoacyl-tRNA synthetase complex-interacting multifunctional Protein 1), TNF-α, IL-10 and CA-19-9 secreted in the serum of normal controls and colon cancer patients were analyzed using an enzyme immunoassay kit according to the manufacturer's instructions, respectively. The amount of protein secretion was measured using a microplate reader (TECAN). The manufacturers of each serum protein assay kit are as follows:

GRS, HRS, WRS ELISA kit (Cusabio, China)
AIMP1 ELISA kit (Elab science, China)
KRS ELISA kit (Mybiosource, USA)
TNF-a, IL-10 (BD science, USA)
CA 19-9 (Abnova, Taiwan).

3. Statistical Analysis

The P value between the proteins secreted in the serum of normal controls and colon cancer patients was analyzed using the Mann-Whitney test/Two-tailed test with XLASTAT software. Dotblot plot, ROC curve, AUC, and standard deviation were analyzed using Graphpad Prism 6 software.

Results

Example 1: Serum Analysis of Normal Controls and Colon Cancer Patients

To search for markers specific for colon cancer, serum proteins were analyzed by enzyme-linked immunosorbent assay (ELISA) for 32 normal controls and 164 colon cancer patients.

The results are shown in Table 2 and FIGS. 1A to 1H, respectively.

TABLE 2

Serum Protein Analysis of Normal controls and Colon Cancer Patients

| (pg/ml) | Normal controls | Colon cancer patients |
|---|---|---|
| GRS | 561.2 ± 137.3 | 535.5 ± 39.08 |
| KRS | 775.6 ± 53.4 | 507 ± 561.1 |
| WRS | 2345 ± 276.2 | 2628 ± 115.6 |
| HRS | 1574 ± 290.1 | 1302 ± 55.33 |
| AIMP1 | 1711 ± 143.5 | 2600 ± 68.32 |
| TNF-α | 142.5 ± 20.01 | 113.6 ± 5.092 |
| IL-10 | 87.40 ± 13.17 | 167.9 ± 4.54 |
| CA 19-9 | 76.63 ± 11.80 | 284.3 ± 48.03 |

As shown in Table 2 and FIGS. 1A to 1H, the levels of KRS (lysyl-tRNA synthetase) and AIMP1 (aminoacyl-tRNA synthetase complex-interacting multifunctional protein 1) proteins were significantly increased in the serum of the colon cancer patients compared with those of normal controls. In particular, KRS was found to be significantly superior to CA 19-9, one of the conventional colon cancer diagnostic markers.

Example 2: ROC Curve Assay

Figure 2A:
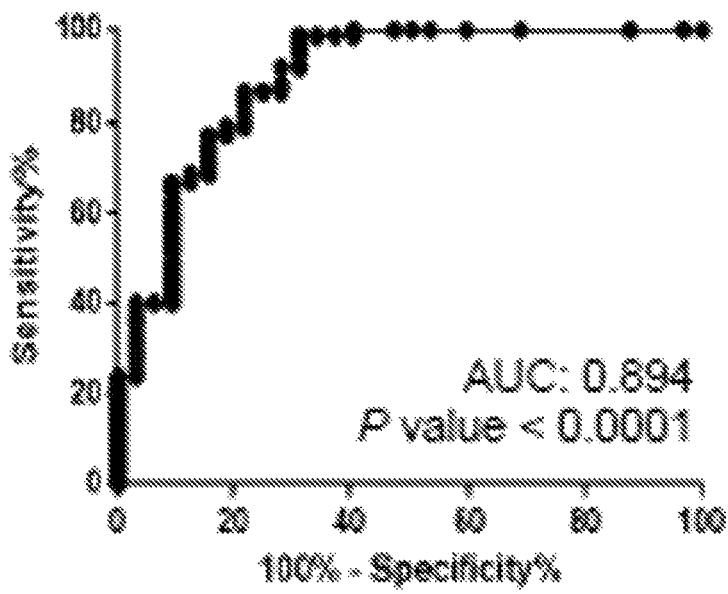
FIGS. 2A, 2B and 2C are graphs showing an ROC curve of serum protein levels.
Figure 2B:
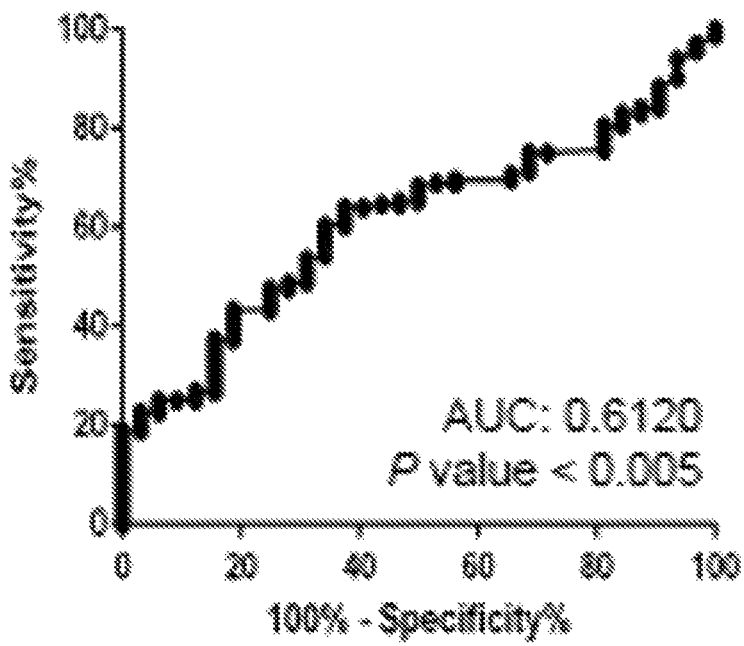
Figure 2C:
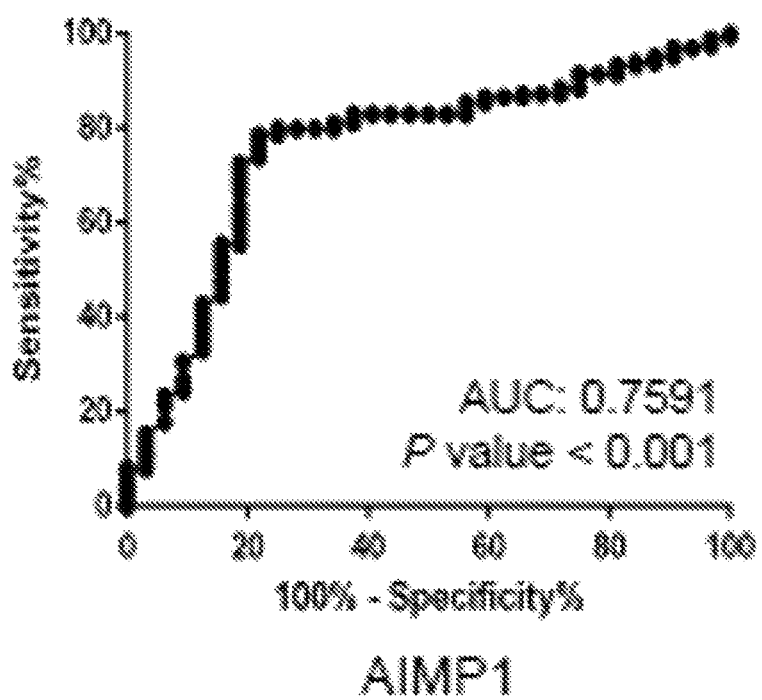

As shown in FIGS. 2A to 2C, the AUC of KRS and AIMP1 ROC is greater than 0.6 with p value of less than 0.01, verifying that the KRS and AIMP1 are excellent colon cancer markers since the levels of KRS and AIMP1 in the serum of the colon cancer patients were statistically significantly higher than those of normal controls. In addition, KRS and AIMP1 were found to be better markers than CA-19-9, a conventional biomarker of colon cancer.

INDUSTRIAL AVAILABILITY

The colon cancer diagnostic markers of KRS and AIMP1 according to the present invention are found to have increased expression levels in the serum of colon cancer patients compared with the normal control. Therefore, by measuring the expression levels of at least one markers selected from the group consisting of KRS and AIMP1, the presence or absence of colon cancer can be accurately and rapidly verified. Thus, the colon cancer diagnostic markers according to the present invention are considered to have excellent industrial applicability.

---

What is claimed is:

1. A method for treating a colon cancer in a subject, the method comprising the steps of:
   (a) obtaining a cell-free sample from a subject suspected of having colon cancer;
   (b) measuring the level the secreted form of lysyl-tRNA synthetase (KRS) and/or aminoacyl-tRNA synthetase complex-interacting multifunctional protein 1 (AIMP1) in the sample;
   (c) identifying the subject as having an increased level of secreted KRS and/or AIMP1 in the cell-free sample, relative to a normal control sample of a healthy subject;
   (d) diagnosing the subject with a colon cancer; and
   (e) treating the diagnosed subject by at least one of (i) administering an effective amount of a therapeutic agent for colon cancer to the diagnosed subject, (ii) conducting a curative surgery, and (iii) conducting a radiation therapy.

2. The method of claim 1, wherein the sample is selected from the group consisting of plasma and serum.

3. The method of claim 1, wherein the protein level is measured by one selected from the group consisting of Western blotting, ELISA, radioimmunoassay, radial immunodiffusion assay, Ouchterlony immunodiffusion, rocket immunoelectrophoresis, immunohistochemistry, Immunoprecipitation assay, complement fixation assay, FACS and protein chip method.

4. A method for screening an anti-colon cancer agent, the method comprising the steps of:
   (a) administering an anti-colon cancer agent candidate to a sample obtained from a colon cancer patient;
   (b) measuring a protein level of at least one secreted protein selected from the group consisting of lysyl-tRNA synthetase (KRS) and aminoacyl-tRNA synthetase complex-interacting multifunctional protein 1 (AIMP1) in the sample under the presence or absence of the anti-colon cancer agent candidate;
   (c) comparing the protein level under the presence of the candidate with the mRNA or protein level under the absence of the candidate;
   (d) selecting the candidate that decreases the protein level under the presence of the candidate; and
   (e) determining the anticancer activity of the selected candidate in a cell or an animal.

5. The method of claim 1, wherein the step of measuring the protein level comprises using an antibody specific for the KRS or AIMP1 protein.

6. The method of claim 1, wherein the KRS protein comprises the amino acid sequence of SEQ ID NO: 3 and the AIMP1 protein comprises the amino acid sequence of SEQ ID NO: 4.

7. The method of claim 1, wherein the measuring step uses a kit containing an agent for measuring a protein level of at least one secreted protein selected from the group consisting of lysyl-tRNA synthetase (KRS) and aminoacyl-tRNA synthetase complex-interacting multifunctional protein 1 (AIMP1).

8. The method of claim 7, wherein the kit is RT-PCR kit, DNA chip kit or a protein chip kit.

* * * * *

SEQUENCE LISTING

<160> NUMBER OF SEQ ID NOS: 8

<210> SEQ ID NO 1
<211> LENGTH: 1794
<212> TYPE: DNA
<213> ORGANISM: Homo sapiens

<400> SEQUENCE: 1

```
atggcggccg tgcaggcggc cgaggtgaaa gtggatggca gcgagccgaa actgagcaag      60
aatgagctga agagacgcct gaaagctgag aagaaagtag cagagaagga ggccaaacag     120
aaagagctca gtgagaaaca gctaagccaa gccactgctg ctgccaccaa ccacaccact     180
gataatggtg tgggtcctga ggaagagagc gtggacccaa atcaatacta caaaatccgc     240
agtcaagcaa ttcatcagct gaaggtcaat ggggaagacc catacccaca caagttccat     300
gtagacatct cactcactga cttcatccaa aaatatagtc acctgcagcc tggggatcac     360
ctgactgaca tcaccttaaa ggtggcaggt aggatccatg ccaaaagagc ttctggggga     420
aagctcatct tctatgatct tcgaggagag ggggtgaagt tgcaagtcat ggccaattcc     480
agaaattata aatcagaaga agaatttatt catattaata acaaactgcg tcggggagac     540
ataattggag ttcaggggaa tcctggtaaa accaagaagg gtgagctgag catcattccg     600
tatgagatca cactgctgtc tccctgtttg catatgttac ctcatcttca ctttgggctc     660
aaagacaagg aaacaaggta tcgccagaga tacttggact tgatcctgaa tgactttgtg     720
aggcagaaat ttatcatccg ctctaagatc atcacatata taagaagttt cttagatgag     780
ctgggattcc tagagattga aactcccatg atgaacatca tcccagggg agccgtggcc     840
```

```
aagcctttca tcacttatca caacgagctg acatgaact tatatatgag aattgctcca      900
gaactctatc ataagatgct tgtggttggt ggcatcgacc gggtttatga aattggacgc      960
cagttccgga atgaggggat tgatttgacg cacaatcctg agttcaccac ctgtgagttc     1020
tacatggcct atgcagacta tcacgatctc atggaaatca cggagaagat ggtttcaggg     1080
atggtgaagc atattacagg cagttacaag gtcacctacc acccagatgg cccagagggc     1140
caagcctacg atgttgactt caccccaccc ttccggcgaa tcaacatggt agaagagctt     1200
gagaaagccc tggggatgaa gctgccagaa acgaacctct ttgaaactga gaaactcgc      1260 aaaattcttg atgatatctg tgtggcaaaa gctgttgaat gccctccacc tcggaccaca     1320
gccaggctcc ttgacaagct tgttggggag ttcctggaag tgacttgcat caatcctaca     1380
ttcatctgtg atcacccaca gataatgagc cctttggcta atggcaccg ctctaaagag      1440 ggtctgactg agcgctttga gctgtttgtc atgaagaaag agatatgcaa tgcgtatact     1500
gagctgaatg atcccatgcg gcagcggcag cttttttgaag aacaggccaa ggccaaggct    1560
gcaggtgatg atgaggccat gttcatagat gaaaacttct gtactgccct ggaatatggg     1620
ctgcccccca cagctggctg gggcatgggc attgatcgag tcgccatgtt tctcacggac     1680
tccaacaaca tcaaggaagt acttctgttt cctgccatga aacccgaaga caagaaggag     1740
aatgtagcaa ccactgatac actggaaagc acaacagttg cacttctgt ctag            1794

<210> SEQ ID NO 2
<211> LENGTH: 939
<212> TYPE: DNA
<213> ORGANISM: Homo sapiens

<400> SEQUENCE: 2
atggcaaata atgatgctgt tctgaagaga ctggagcaga agggtgcaga ggcagatcaa       60
atcattgaat atcttaagca gcaagttcct ctacttaagg agaaagcaat tttgcaggca      120
actttgaggg aagagaagaa acttcgagtt gaaaatgcta aactgaagaa agaaattgaa      180 gaactgaaaac aagagctaat tcaggcagaa attcaaaatg gagtgaagca ataccatt      240 ccatctggta ctcccactgca cgctaattct atggtttctg aaaatgtgat acagtctaca      300
gcagtaacaa ccgtatcttc tggtaccaaa gaacagataa aggaggaac aggagacgaa      360 aagaaagcga agagaaaat tgaaaagaaa ggagagaaga aggagaaaaa acagcaatca      420
atagctggaa gtgccgactc taagccaata gatgtttccc gtctggatct tcgaattggt      480
tgcatcataa ctgctagaaa acaccctgat gcagattctt tgtatgtgga agaagtagat      540
gtcggagaaa tagccccaag gacagttgtc agtggcctgg tgaatcatgt tcctcttgaa      600
cagatgcaaa atcggatggt gattttactt tgtaacctga acctgcaaa gatgagggga       660 gtattatctc aagcaatggt catgtgtgct agttcaccag agaaaattga atcttggct       720 cctccaaatg ggtctgttcc tggagacaga attactttg atgctttccc aggagagcct       780
gacaaggagc tgaatcctaa gagaagatt tgggagcaga tccagcctga tcttcacact      840
aatgatgagt gtgtggctac atacaaagga gttccctttg aggtgaaagg aagggagta      900 tgtagggctc aaaccatgag caacagtgga atcaaataa                             939

<210> SEQ ID NO 3
<211> LENGTH: 597
<212> TYPE: PRT
<213> ORGANISM: Homo sapiens

<400> SEQUENCE: 3
```

```
Met Ala Ala Val Gln Ala Ala Glu Val Lys Val Asp Gly Ser Glu Pro
1               5                   10                  15

Lys Leu Ser Lys Asn Glu Leu Lys Arg Arg Leu Lys Ala Glu Lys Lys
            20                  25                  30

Val Ala Glu Lys Glu Ala Lys Gln Lys Glu Leu Ser Gly Lys Gln Leu
        35                  40                  45

Ser Gln Ala Thr Ala Ala Thr Asn His Thr Thr Asp Asn Gly Val
    50                  55                  60

Gly Pro Glu Glu Glu Ser Val Asp Pro Asn Gln Tyr Tyr Lys Ile Arg
65                  70                  75                  80

Ser Gln Ala Ile His Gln Leu Lys Val Asn Gly Glu Asp Pro Tyr Pro
                85                  90                  95

His Lys Phe His Val Asp Ile Ser Leu Thr Asp Phe Ile Gln Lys Tyr
            100                 105                 110

Ser His Leu Gln Pro Gly Asp His Leu Thr Asp Ile Thr Leu Lys Val
        115                 120                 125

Ala Gly Arg Ile His Ala Lys Arg Ala Ser Gly Lys Leu Ile Phe
    130                 135                 140

Tyr Asp Leu Arg Gly Glu Gly Val Lys Leu Gln Val Met Ala Asn Ser
145                 150                 155                 160

Arg Asn Tyr Lys Ser Glu Glu Phe Ile His Ile Asn Asn Lys Leu
                165                 170                 175

Arg Arg Gly Asp Ile Ile Gly Val Gln Gly Asn Pro Gly Lys Thr Lys
            180                 185                 190

Lys Gly Glu Leu Ser Ile Ile Pro Tyr Glu Ile Thr Leu Leu Ser Pro
        195                 200                 205

Cys Leu His Met Leu Pro His Leu His Phe Gly Leu Lys Asp Lys Glu
    210                 215                 220

Thr Arg Tyr Arg Gln Arg Tyr Leu Asp Leu Ile Leu Asn Asp Phe Val
225                 230                 235                 240

Arg Gln Lys Phe Ile Ile Arg Ser Lys Ile Ile Thr Tyr Ile Arg Ser
                245                 250                 255

Phe Leu Asp Glu Leu Gly Phe Leu Glu Ile Glu Thr Pro Met Met Asn
            260                 265                 270

Ile Ile Pro Gly Gly Ala Val Ala Lys Pro Phe Ile Thr Tyr His Asn
        275                 280                 285

Glu Leu Asp Met Asn Leu Tyr Met Arg Ile Ala Pro Glu Leu Tyr His
    290                 295                 300

Lys Met Leu Val Val Gly Gly Ile Asp Arg Val Tyr Glu Ile Gly Arg
305                 310                 315                 320

Gln Phe Arg Asn Glu Gly Ile Asp Leu Thr His Asn Pro Glu Phe Thr
                325                 330                 335

Thr Cys Glu Phe Tyr Met Ala Tyr Ala Asp Tyr His Asp Leu Met Glu
            340                 345                 350

Ile Thr Glu Lys Met Val Ser Gly Met Val Lys His Ile Thr Gly Ser
        355                 360                 365

Tyr Lys Val Thr Tyr His Pro Asp Gly Pro Glu Gly Gln Ala Tyr Asp
    370                 375                 380

Val Asp Phe Thr Pro Pro Phe Arg Arg Ile Asn Met Val Glu Glu Leu
385                 390                 395                 400

Glu Lys Ala Leu Gly Met Lys Leu Pro Glu Thr Asn Leu Phe Glu Thr
                405                 410                 415
```

```
Glu Glu Thr Arg Lys Ile Leu Asp Asp Ile Cys Val Ala Lys Ala Val
            420                 425                 430

Glu Cys Pro Pro Arg Thr Thr Ala Arg Leu Leu Asp Lys Leu Val
        435                 440                 445

Gly Glu Phe Leu Glu Val Thr Cys Ile Asn Pro Thr Phe Ile Cys Asp
        450                 455                 460

His Pro Gln Ile Met Ser Pro Leu Ala Lys Trp His Arg Ser Lys Glu
465                 470                 475                 480

Gly Leu Thr Glu Arg Phe Glu Leu Phe Val Met Lys Lys Glu Ile Cys
            485                 490                 495

Asn Ala Tyr Thr Glu Leu Asn Asp Pro Met Arg Gln Arg Gln Leu Phe
            500                 505                 510

Glu Glu Gln Ala Lys Ala Lys Ala Ala Gly Asp Asp Glu Ala Met Phe
        515                 520                 525

Ile Asp Glu Asn Phe Cys Thr Ala Leu Glu Tyr Gly Leu Pro Pro Thr
        530                 535                 540

Ala Gly Trp Gly Met Gly Ile Asp Arg Val Ala Met Phe Leu Thr Asp
545                 550                 555                 560

Ser Asn Asn Ile Lys Glu Val Leu Leu Phe Pro Ala Met Lys Pro Glu
            565                 570                 575

Asp Lys Lys Glu Asn Val Ala Thr Thr Asp Thr Leu Glu Ser Thr Thr
            580                 585                 590

Val Gly Thr Ser Val
        595

<210> SEQ ID NO 4
<211> LENGTH: 312
<212> TYPE: PRT
<213> ORGANISM: Homo sapiens

<400> SEQUENCE: 4

Met Ala Asn Asn Asp Ala Val Leu Lys Arg Leu Glu Gln Lys Gly Ala
1               5                   10                  15

Glu Ala Asp Gln Ile Ile Glu Tyr Leu Lys Gln Gln Val Ser Leu Leu
            20                  25                  30

Lys Glu Lys Ala Ile Leu Gln Ala Thr Leu Arg Glu Glu Lys Lys Leu
        35                  40                  45

Arg Val Glu Asn Ala Lys Leu Lys Lys Glu Ile Glu Glu Leu Lys Gln
    50                  55                  60

Glu Leu Ile Gln Ala Glu Ile Gln Asn Gly Val Lys Gln Ile Pro Phe
65                  70                  75                  80

Pro Ser Gly Thr Pro Leu His Ala Asn Ser Met Val Ser Glu Asn Val
            85                  90                  95

Ile Gln Ser Thr Ala Val Thr Thr Val Ser Ser Gly Thr Lys Glu Gln
            100                 105                 110

Ile Lys Gly Gly Thr Gly Asp Glu Lys Lys Ala Lys Glu Lys Ile Glu
        115                 120                 125

Lys Lys Gly Glu Lys Lys Glu Lys Gln Gln Ser Ile Ala Gly Ser
        130                 135                 140

Ala Asp Ser Lys Pro Ile Asp Val Ser Arg Leu Asp Leu Arg Ile Gly
145                 150                 155                 160

Cys Ile Ile Thr Ala Arg Lys His Pro Asp Ala Asp Ser Leu Tyr Val
            165                 170                 175

Glu Glu Val Asp Val Gly Glu Ile Ala Pro Arg Thr Val Val Ser Gly
            180                 185                 190
```

```
Leu Val Asn His Val Pro Leu Glu Gln Met Gln Asn Arg Met Val Ile
    195                 200                 205

Leu Leu Cys Asn Leu Lys Pro Ala Lys Met Arg Gly Val Leu Ser Gln
    210                 215                 220

Ala Met Val Met Cys Ala Ser Ser Pro Glu Lys Ile Glu Ile Leu Ala
225                 230                 235                 240

Pro Pro Asn Gly Ser Val Pro Gly Asp Arg Ile Thr Phe Asp Ala Phe
                245                 250                 255

Pro Gly Glu Pro Asp Lys Glu Leu Asn Pro Lys Lys Ile Trp Glu
                260                 265                 270

Gln Ile Gln Pro Asp Leu His Thr Asn Asp Glu Cys Val Ala Thr Tyr
                275                 280                 285

Lys Gly Val Pro Phe Glu Val Lys Gly Lys Gly Val Cys Arg Ala Gln
                290                 295                 300

Thr Met Ser Asn Ser Gly Ile Lys
305                 310

<210> SEQ ID NO 5
<211> LENGTH: 21
<212> TYPE: DNA
<213> ORGANISM: Artificial Sequence
<220> FEATURE:
<223> OTHER INFORMATION: Human KRS forward primer

<400> SEQUENCE: 5
aggaaacaag gtatcgccag a                                              21

<210> SEQ ID NO 6
<211> LENGTH: 22
<212> TYPE: DNA
<213> ORGANISM: Artificial Sequence
<220> FEATURE:
<223> OTHER INFORMATION: Human AIMP1 forward primer

<400> SEQUENCE: 6
ctggtgaatc atgttcctct tg                                             22

<210> SEQ ID NO 7
<211> LENGTH: 23
<212> TYPE: DNA
<213> ORGANISM: Artificial Sequence
<220> FEATURE:
<223> OTHER INFORMATION: Human KRS reverse primer

<400> SEQUENCE: 7
cagctcgttg tgataagtga tga                                            23

<210> SEQ ID NO 8
<211> LENGTH: 25
<212> TYPE: DNA
<213> ORGANISM: Artificial Sequence
<220> FEATURE:
<223> OTHER INFORMATION: Human AIMP1 reverse primer

<400> SEQUENCE: 8
ggaaagcatc aaaagtaatt ctgtc                                          25
```